United States Patent
Mas Marfany

(10) Patent No.: US 6,523,537 B1
(45) Date of Patent: Feb. 25, 2003

(54) AUTOMATIC CONTROL METHOD FOR SUPPLYING ANAESTHETIC TO A LOW FLOW-TYPE CLOSED CIRCUIT

(76) Inventor: Jaime Mas Marfany, Rius i Paulet 93, casa 4–08190 Sant Cugat del Valles (ES)

( * ) Notice: Subject to any disclaimer, the term of this patent is extended or adjusted under 35 U.S.C. 154(b) by 0 days.

(21) Appl. No.: 09/673,525
(22) PCT Filed: Apr. 14, 1999
(86) PCT No.: PCT/ES99/00095

§ 371 (c)(1),
(2), (4) Date: Dec. 4, 2000

(87) PCT Pub. No.: WO99/52580

PCT Pub. Date: Oct. 21, 1999

(30) Foreign Application Priority Data

Apr. 14, 1998 (ES) .............................................. 9800782

(51) Int. Cl.[7] ............................................. A61M 15/00
(52) U.S. Cl. .............................. 128/203.12; 128/203.14
(58) Field of Search ...................... 128/204.18, 204.19, 128/204.21, 204.22, 204.23, 204.26, 204.29, 205.11, 205.13–205.15, 203.12–203.15, 200.24

(56) References Cited

U.S. PATENT DOCUMENTS

| | | | | |
|---|---|---|---|---|
| 3,575,168 A | * | 4/1971 | Jones et al. | 128/203.14 |
| 4,444,182 A | * | 4/1984 | Gregory | 128/203.14 |
| 4,651,729 A | * | 3/1987 | Rae | 128/203.14 |
| 4,932,398 A | * | 6/1990 | Lancaster et al. | 128/200.14 |
| 5,237,990 A | * | 8/1993 | Psaros et al. | 128/203.12 |
| 5,293,865 A | * | 3/1994 | Altner | 128/202.27 |
| 5,390,665 A | * | 2/1995 | Leach | 128/203.12 |
| 5,520,168 A | * | 5/1996 | Whitaker | 128/202.22 |
| 5,592,934 A | * | 1/1997 | Thwaites | 128/203.12 |
| 5,967,141 A | * | 10/1999 | Heinonen | 128/203.12 |
| 6,131,571 A | * | 10/2000 | Lampotang et al. | 128/204.21 |

FOREIGN PATENT DOCUMENTS

| | | |
|---|---|---|
| DE | 41 09 629 A1 | 9/1992 |
| EP | 0397011 A2 | 11/1990 |
| EP | 0496336 A1 | 7/1992 |
| EP | 0545567 A1 | 6/1993 |
| EP | 0716861 A1 | 6/1996 |
| EP | 0832662 A2 | 4/1998 |
| EP | 0835672 A2 | 4/1998 |
| WO | WO 92/11887 | 7/1992 |

* cited by examiner

*Primary Examiner*—Aaron J. Lewis
*Assistant Examiner*—Teena Mitchell
(74) *Attorney, Agent, or Firm*—Katten Muchin Zavis Rosenman

(57) ABSTRACT

The method comprises the stages of a) setting the ventilatory rate (VR) for the patient; b) automatically setting the flow of fresh gas (FFG) to 10% of the VR; c) determining the volatile anaesthetic fractions inhaled (% IF) and exhaled (% EF); d) opening the dial of the anaesthetic vaporiser to the value resulting from multiplying the differential (% IF–% EF) by 10; e) supplying the circuit with a quantity of anaesthetic that covers, at least, the total quantity of anaesthetic consumed by the patient, by means of opening the dial of the anaesthetic vaporiser; and f) mixing the quantity of anaesthetic with the FFG before introducing the mixture into the patient. The method has application in the administration of inhaled anaesthetics in low-flow anaesthetic systems.

4 Claims, 3 Drawing Sheets

AUTOMATIC CONTROL METHOD FOR SUPPLYING ANAESTHETIC TO A LOW FLOW-TYPE CLOSED CIRCUIT

FIELD OF THE INVENTION

The invention relates to the automatic control of supply of volatile anaesthetic to a closed circuit at low flow rates.

BACKGROUND OF THE INVENTION

A closed circuit of anaesthetic is an anaesthetic system based on the re-administration of exhaled gases, from which carbon dioxide has been absorbed, to which oxygen is added and the anaesthetics consumed.

As is known, the concentration of volatile anaesthetic in an anaesthetic circuit is determined by the anaesthetist as he or she wishes and in accordance with the Minimum Alveolar Concentration (M.A.C.) for each anaesthetic.

Changes to this M.A.C. are those which, classically, in a circuit of low flow, are modified by varying the flow of fresh gas and, therefore, the amount of volatile anaesthetic dragged along by the current of fresh gas. This way of controlling the anaesthetic presents some difficulties, among which the excessive consumption of anaesthetic can be mentioned.

Now it has been found that the concentration of anaesthetic can advantageously be regulated by modifying the dial of the anaesthetic vaporiser instead of modifying the flow of fresh gas. This way of controlling the concentration of anaesthetic has, among other advantages, that of reducing the consumption of anaesthetic.

DESCRIPTION OF THE REFERENCE NUMERALS

Figure 1:
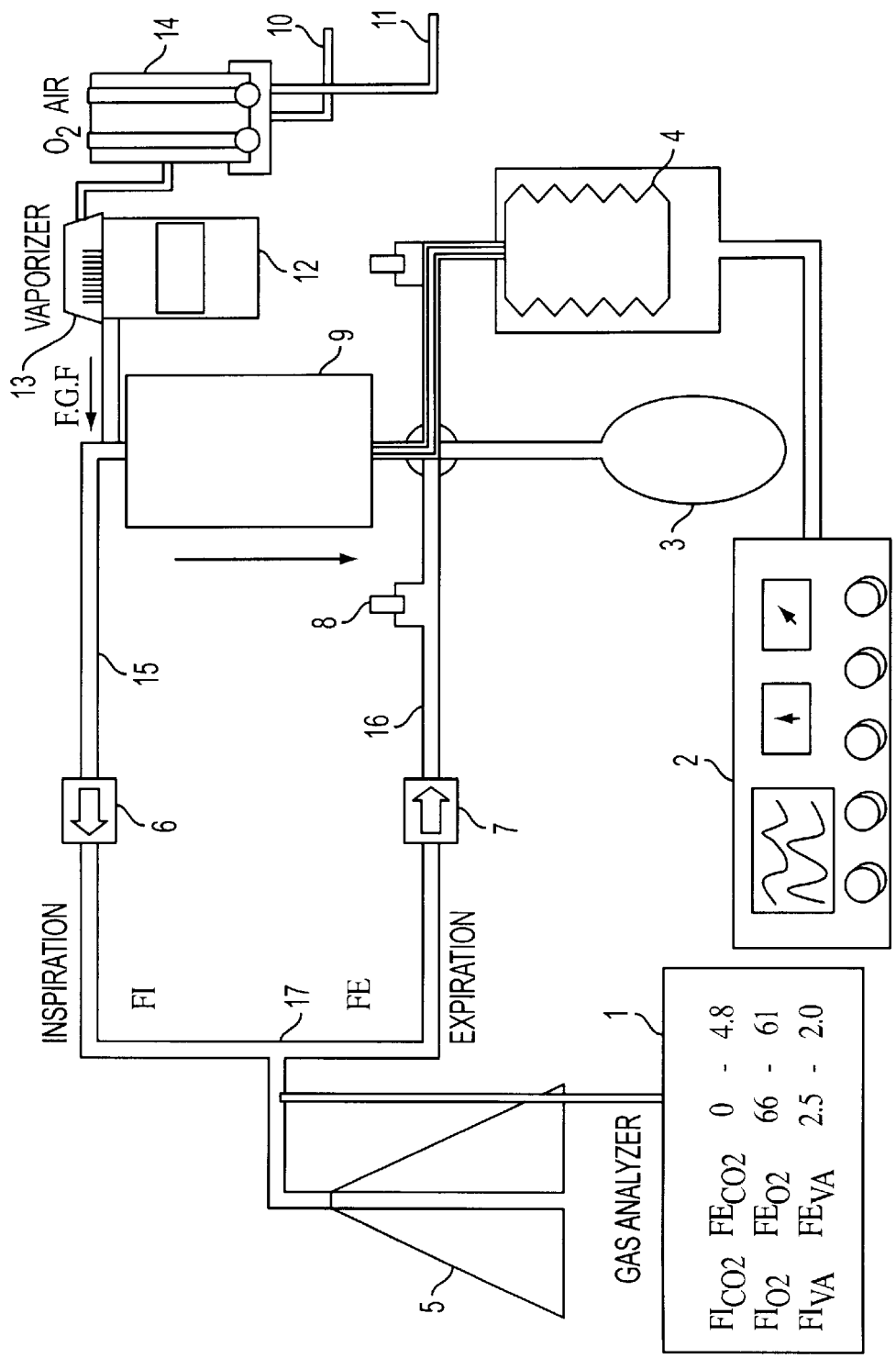
FIG. 1 illustrates an initial phase of filling the closed circuit.

1. Gas analyser
2. Mechanic ventilator.
3. Reservoir ball or bag for manual ventilation
4. Concertina
5. Patient's lungs
6. Inhaling branch unidirectional valve
7. Exhaling branch unidirectional valve
8. Adjustable valve for expulsing excess gas or "pop-off".
9. Canister
10. $O_2$ intake
11. Air intake
12. Vaporiser
13. Dial of the vaporiser
14. Rotameters
15. Inhaling branch
16. Exhaling branch
17. "Y" or "T" junction.

DETAILED DESCRIPTION OF THE INVENTION

This invention relates to a method of automatic control for the supply of a volatile anaesthetic to a closed circuit at low flow rates.

The automatic control method for the supply of a volatile anaesthetic to a closed anaesthetic circuit, object of this invention, that comprises the stage of mixing the fresh gas and the volatile anaesthetic before being introduced into the patient, is characterised because:

a) the ventilatory rate of the patient is set;

b) the flow of fresh gas is set automatically to 10% of the set ventilatory rate;

c) the fraction inhaled (% IF) and exhaled (% EF) by the patient of volatile anaesthetic are determined;

d) the dial of the anaesthetic vaporiser is set to the value resulting from multiplying by 10 the differential of the fraction inhaled (% IF) and fraction exhaled (% EF) of volatile anaesthetic by the patient, that is to say, % dial=(% IF−% EF)×10, changing, in the same proportion, the opening of said dial every time that said differential of inhaled fraction (% IF) and exhaled fraction (% EF) of volatile anaesthetic by the patient varies e) a quantity of anaesthetic is supplied to the circuit that covers, at least, the total amount of anaesthetic consumed by the patient, by means of the opening of the anaesthetic vaporiser dial; and f) the quantity of anaesthetic is mixed with the flow of fresh gas before being introduced into the patient.

In the sense used in this description, a closed circuit of anaesthetic at low flows refers to an anaesthetic system based on the re-administration of the exhaled gases, from which the carbon dioxide has been absorbed, and to which oxygen and the anaesthetics consumed are added, and in which the total flow of fresh gas (oxygen) is less than 4 l/min.

Figure 2:
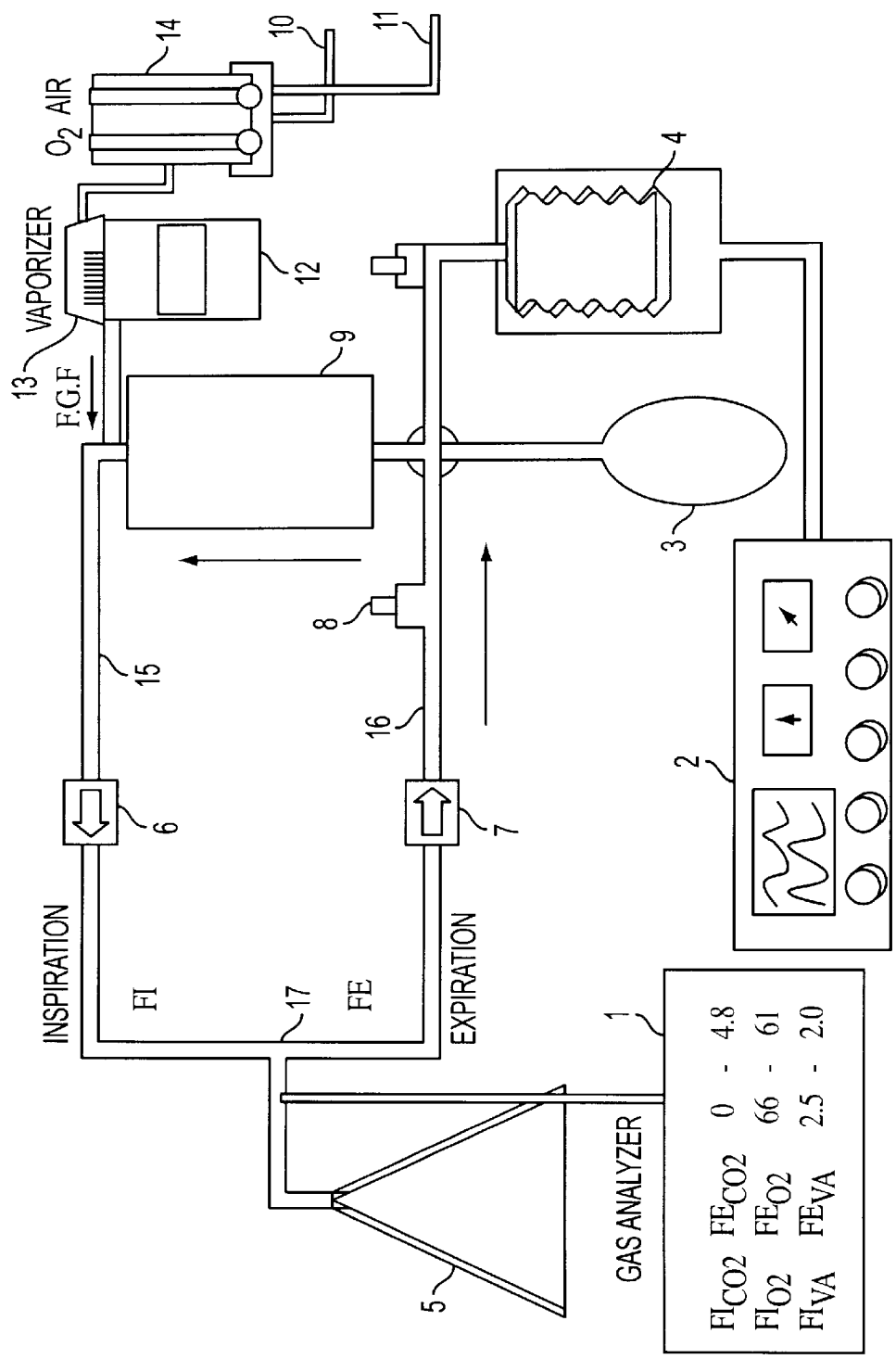
FIG. 2 illustrates an inhaling phase.
Figure 3:
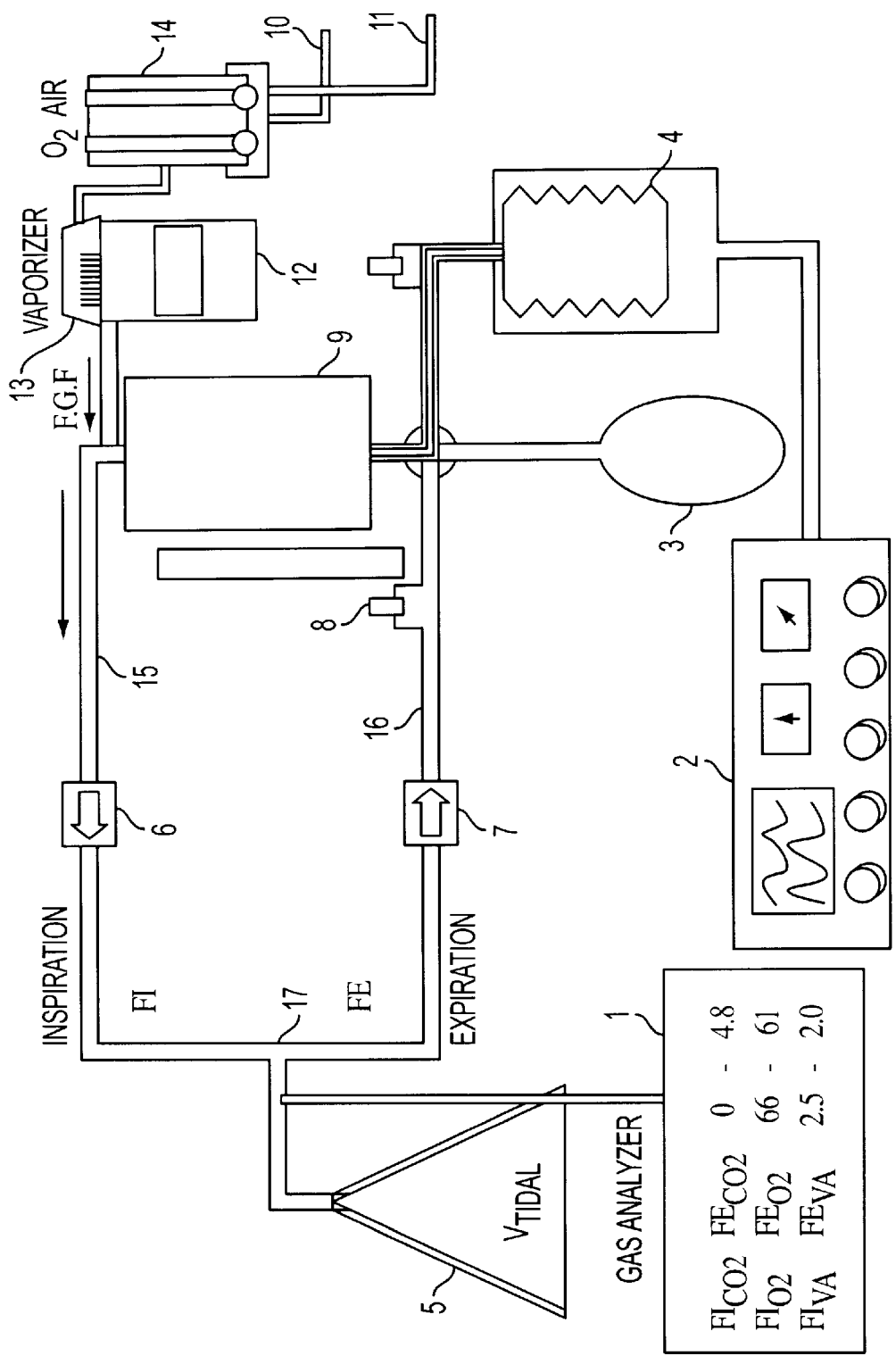
FIG. 3 illustrates an exhaling phase.

A typical closed anaesthetic circuit is illustrated in FIGS. 1–3, designed for working with volatile anaesthetics and which can operate at low flow rates, in which the method of automatic control of volatile anaesthetic, object of this invention, can be applied, is comprised of the following elements: source of fresh gas 14;

a source of volatile anaesthetic that contains a vaporiser 12 that incorporates a dial 13 for regulating the anaesthetic output, in such a way that the anaesthetic is vaporised before being mixed and dragged along by the fresh gas;

an input of fresh gas carrying the volatile anaesthetic;

two tubes that constitute the inhaling and exhaling branches 15, 16 respectively of the circuit;

two unidirectional valves, one of which 6 is on the inhaling branch 15 and the other 7 is on the exhaling branch 16, that determine the direction of flow within the circuit;

an adjustable valve 8 for expulsing excess gas;

a piece 17 in the form of a "Y" or a "T" for connection to the aerial pathway of the patient;

a reservoir ball or bag 3, with capacity greater than the flow volume, adaptable or which can be substituted by the concertina 4 of a ventilator 2; and a canister or carbon dioxide absorbing device 9.

While exhaling (see FIG. 3), the inhaling valve 6 is closed and the exhaled gases are transferred to the balloon, where the fresh gases which are entering the system at this time also arrive, the excess of gas from the patient is expelled outside via the adjustable valve for expulsion of excess gas 8.

While inhaling (see FIG. 2), the exhaling valve 7 is closed, the inhaling valve 6 is opened and the patient receives the fresh gas that is entering in the circuit at this time, the fresh gas that occupied the canister 9 during exhaling and the exhaled gas contained in the balloon which is stripped of its carbon dioxide as the gas passes through the canister 9.

The term "patient", as it is used in this description, includes any subject, person or animal, who receives volatile anaesthetic.

As volatile anaesthetic any known inhaled volatile anaesthetics can be used, for example, halogenated inhaled anaesthetics such as halothane, desflurane, isoflurane and sevoflurane.

The method of the invention starts by setting the ventilatory rate (VR) to be breathed by the patient. This is the quantity of air that enters and leaves the lungs of the patient in one minute, and is set by adjusting the ventilator to the desired ventilatory rate. The VR is equal to the sum of the alveolar volume [part of the VR that arrives at the alveoli and serves for hematosis or gas exchange (oxygen, carbon dioxide and anaethetic)] and the dead volume [quantity of air that enters and leaves the lungs without reaching the pulmonary alveoli, that is to say, without gas exchange].

Once the VR has been established, the flow of fresh gas is automatically set. The fresh gas consists only of oxygen and serves as a vehicle for introducing the volatile anaesthetic, in vapour form, into the circuit and then into the patient. The flow of fresh gas has to cover the needs of the oxygen consumed, that is to say, the quantity of oxygen necessary for maintaining the basal metabolic consumption. In general, said oxygen consumption can be calculated from the formula [1]:

$$\text{Oxygen consumption} = \text{weight (kg)}^{3/4} \times 10 \qquad [1]$$

The result obtained from applying formula [1] normally ranges between 200 and 300 ml/min, which means a supply of 500 ml/min of oxygen to a closed anaesthetic circuit. This circuit normally has a capacity of 4 or 5 litres, filled with oxygen at 100%, thus guaranteeing that any oxygen consumption needs are covered.

In the method of the present invention, the flow of fresh gas (FFG) is set automatically to 10% of the established ventilatory rate (VR), that is to say, FFG=10% X VR.

The fraction of anaesthetic inhaled by the patient (% IF) is the percentage of the volatile anaesthetic that the ventilator administers on each inhalation. This can be determined by a suitable piece of equipment using any conventional technique appropriate for quantifying the gases that make up the fraction inhaled by the patient.

The fraction exhaled by the anaesthetised patient (% EF) is the percentage of volatile anaesthetic that is measured in the exhaling branch of the circuit, that is to say, the quantity of anaesthetic that leaves the lung of the patient once a certain quantity of the inhaled fraction has been captured by the anaesthetised patient (% IF). The fraction exhaled by the anaesthetised patient can be determined by means of suitable equipment using any conventional technique suitable for determining and quantifying the gases that constitute the fraction exhaled by the patient, including the carbon dioxide levels.

Next, in accordance with the method of this invention, the dial of the vaporiser of the volatile anaesthetic is opened to the value corresponding to multiplying by 10 the differential of the fractions inhaled (% IF) and exhaled (% EF) by the anaesthetised patient, that is to say, the dial opening corresponds to the result of carrying out the operation (% IF–% EF)×10, thus establishing the equilibrium that is shown in equation [4] (see later).

Every time that the differential (% IF–% EF) varies in time, for example, due to variations in capture of anaesthetic by the patient, the vaporiser dial should changed in exactly in this same direction such that the concentration pre-established by the anaesthetist (M.A.C.) does not vary in time (dynamic stability of the circuit).

Next, by means of opening the dial of the anaesthetic dial a quantity of volatile anaesthetic is supplied to the low-flow closed anaesthetic circuit that covers, at least, the total quantity of anaesthetic consumed by the patient, a quantity that is determined by equation [2]:

$$TQAC = (\% \ IF - \% \ EF) \times V_{ALV} \qquad [2]$$

Where
  TQAC is the total quantity of anaesthetic consumed by the patient;
  % IF is the fraction inhaled by the anaesthetised patient;
  % EF is the fraction exhaled by the anaesthetised patient; and
  $V_{ALV}$ is the alveolar volume of ventilation.

Said quantity of anaesthetic consumed by the patient is derived from the amount of anaesthetic supplied to the circuit that, in a particular embodiment of the invention, can be determined by equation [3]:

$$QASC = FFG \times \% \ \text{dial} \qquad [3]$$

Where
  QASC is th e quantity of anaesthetic supplied to the circuit;
  FFG is the flow of fresh gas; and
  % dial represents the concentration of anaesthetic at the output of the anaesthetic vaporiser.

In an equilibrium situation, the quantity of anaesthetic supplied to the circuit (QASC) is equal to the total quantity of anaesthetic consumed (TQAC), thus equations [2] and [3] become equivalent, giving equation [4]:

$$(\% \ IF - \% \ EF) \times V_{ALV} = FFG \times \% \ \text{dial} \qquad [4]$$

where % IF, % EF, $V_{ALV}$, FFG and % dial have the meanings indicated hereinabove.

Equation [4] reflects the pharmacodynamic equilibrium of a closed circuit when nothing is released to the outside. As can be appreciated in equation [4], when the system is in equilibrium, the total anaesthetic consumed (left part of equation [4]) is equal to the volume of volatile anaesthetic supplied to the circuit (right part of equation [4]).

However, normally a loss of gas to the outside occurs, given that more flow of fresh gas (oxygen) is always administered than that strictly captured by the patient. Thus, in actual fact, the anaesthetic supplied can be considered as equal to the sum of anaesthetic consumed by the patient and the anaesthetic released to the outside.

Therefore, in a particular embodiment of the method object of this invention, the quantity of anaesthetic supplied to the circuit (QASC) is equal to the total quantity of anaesthetic consumed by the patient plus the quantity of anaesthetic lost to the outside, which can thus be expressed by equation [5]:

$$QASC = (\% \ IF - \% \ EF) \times V_{ALV} + [FFG - ((\%O_{2 \ inh} - \%O_{2 \ exh}) \times VR)] \times \% \ FE \qquad [5]$$
(anaesthetic consumed) (anaesthetic lost)

where
  QASC, % IF, % EF, $V_{ALV}$, FFG and VR have the meanings indicated hereinabove;
  $O_{2 \ inh}$ is the fraction of inhaled oxygen, supplied by the flow of fresh gas; and
  $O_{2 \ exh}$ is the fraction of oxygen exhaled by the patient.

As can be appreciated from equation [5], the more the quantity of oxygen supplied by the fresh gas approaches the quantity of oxygen consumed by the patient, the less the quantity of oxygen lost to the outside, and therefore, the efficiency will be maximum.

The supply of the quantity of anaesthetic to the circuit is effected, according to the present invention, by means of opening the dial of the anaesthetic vaporiser. This constitutes a substantial difference to the classical method of supplying anaesthetic to the circuit, which consists of increasing the flow of fresh gas. Although this achieves a rapid increase in the inhaled fraction, this effect is achieved at the expense of losing through the valve for expulsion all the excess oxygen containing an appreciable concentration of corresponding anaesthetic. The invention provides, in definitive fashion, a considerable saving of anaesthetic because the FFG is never increased and anaesthetic is not lost to the outside. In contrast to that established normally, the present invention makes it clear that modifying the dial opening to vary the concentrations of anaesthetic (and not the flow of fresh gas) an exact, ecological and efficient model is achieved for the supply of anaesthetic to the system.

Finally, the volatile anaesthetic supplied by the vaporiser is mixed with the flow of fresh gas, which drags it along before being introduced into the patient.

The method of the invention is not effected on a human or animal body as it is carried out at a stage prior to the introduction of the anaesthetic into the patient, it is suitable for quantifying, controlling and optimising the bases for a possible automation of a anaesthetic work station that functions with a low-flow circular circuit.

The method of the invention has numerous advantages, which include the following;

low consumption of anaesthetic minimal loss of anaesthetic, because, as the patient does not consume more than 300 ml of oxygen per minute, every time values much larger than this figure are supplied to the system (which takes place when the control of anaesthetic supply to the circuit is effected by increasing the flow of fresh gas), the rest is lost to the outside with a concentration of anaesthetic equal to that of the fraction exhaled by the anaesthetised patient. Controlling the supply of anaesthetic supplied by varying the vaporiser dial, and without increasing the flow of fresh gas above 500 ml of oxygen, the loss of anaesthetic is minimal;

reduction in the emissions to the outside which implies (i) a reduction in the contamination of the operating theatre, contributing to better health in the workplace, and (ii) a reduction in the environmental contamination not only as a result of the considerable reduction in the emission of chlorofluorinated compounds (CFC's) found in some halogenated anaesthetics, which represent, approximately, 0.1% of the total release of CFC's to the atmosphere, thus contributing to a preservation of the ozone layer, but also because due to the fact that the anaesthetic mixture does not contain nitrogen protoxide, a nitrogenated compound that contributes to the greenhouse effect is eliminated;

improvement in the temperature and humidification of the gas breathed in by the patient during anaesthesia, maintaining the values for temperature (28–32° C.) and relative humidity (17–30 mg $H_2O$/l) which are close to the optimal values, given that, as is well known, the higher the flow rate of fresh gas the colder and drier the air breathed in by the patient, which leads to a loss of warmth and a drying of the bronchial mucus; and a contribution to the improvement of the monitoring process thanks to the homogeneity and stability of the mixture of gases breathed in.

What is claimed is:

1. A method of automatic control for the supply of a volatile anaesthetic to a closed anaesthetic circuit of low flow, which comprises the stage of mixing fresh gas and volatile anaesthetic before introducing the mixture into the patient, the method comprising the steps of:

a) setting a ventilatory rate (VR) of the patient;

b) automatically setting a flow of fresh gas (FFG) to 10% of the VR;

c) determining a fraction inhaled (% IF) and exhaled (% EF) by the patient of volatile anaesthetic;

d) setting a dial of an anaesthetic vaporiser to a value resulting from multiplying by 10 a differential of the inhaled fraction (% IF) and exhaled fraction (% EF) of volatile anaesthetic by the patient, wherein a concentration of anaesthetic at an output of the anaesthetic vaporizer (% dial) is equal to (% IF–% EF)×10, and changing, in a same proportion, the opening of said dial every time that said differential of inhaled fraction (% IF) and exhaled fraction (% EF) of volatile anaesthetic by the patient varies;

e) supplying a quantity of anaesthetic to a circuit (QASC) that covers at least a total quantity of anaesthetic consumed by the patient (TQAC) by means of opening of the dial of the anaesthetic vaporizer; and f) mixing the quantity of anaesthetic with the FFG before introducing said mixture into the patient.

2. A method according to claim 1, wherein the TQAC is determined by the equation:

$$TQAC = (\%IF - \%EF) \times V_{ALV}$$

where $V_{ALV}$ is an alveolar volume of ventilation.

3. A method according to claim 1, wherein the QASC is determined by the equation QASC=FFG×% dial.

4. A method according to claim 1, wherein the QASC is determined by the equation:

$$QASC = (\%IF - \%EF) \times V_{ALV} + [FFG - ((\%)O_{2\ inh} - \%O_{2\ exh}) \times VR] \times \%EF$$

where $V_{ALV}$ is an alveolar volume of ventilation;

$\%O_{2\ inh}$ is a fraction of inhaled oxygen, supplied by the FFG; and $\%O_{2\ exh}$ is a fraction of exhaled oxygen.

* * * * *